US011485702B2

United States Patent
Bellini et al.

(10) Patent No.: US 11,485,702 B2
(45) Date of Patent: Nov. 1, 2022

(54) AMINOALKYL (METH)ACRYLATE STABILISATION

(71) Applicant: Arkema France, Colombes (FR)

(72) Inventors: Clement Bellini, Saint Alvold (FR); Yves Cabon, Saint Alvold (FR); Patrice Defer, Saint Alvold (FR)

(73) Assignee: Arkema France, Colombes (FR)

( * ) Notice: Subject to any disclaimer, the term of this patent is extended or adjusted under 35 U.S.C. 154(b) by 110 days.

(21) Appl. No.: 17/283,272

(22) PCT Filed: Sep. 18, 2019

(86) PCT No.: PCT/FR2019/052173
§ 371 (c)(1),
(2) Date: Apr. 7, 2021

(87) PCT Pub. No.: WO2020/070403
PCT Pub. Date: Apr. 9, 2020

(65) Prior Publication Data
US 2021/0380523 A1 Dec. 9, 2021

(30) Foreign Application Priority Data
Oct. 2, 2018 (FR) ...................................... 1859127

(51) Int. Cl.
*C07C 213/10* (2006.01)
*C07C 213/06* (2006.01)

(52) U.S. Cl.
CPC .......... *C07C 213/10* (2013.01); *C07C 213/06* (2013.01)

(58) Field of Classification Search
None
See application file for complete search history.

(56) References Cited

U.S. PATENT DOCUMENTS

| 5,258,138 A | 11/1993 | Gatechair et al. |
| 5,322,960 A | 6/1994 | Sakamoto et al. |
| 5,728,872 A | 3/1998 | Riemenschneider |
| 2004/0168903 A1 | 9/2004 | Geisendoerfer et al. |
| 2004/0171868 A1 | 9/2004 | Geisendoerfer et al. |
| 2004/0249191 A1* | 12/2004 | Schmitt ................ C07C 213/06 560/222 |
| 2008/0161596 A1 | 7/2008 | Riondel et al. |

FOREIGN PATENT DOCUMENTS

| DE | 19956509 | 1/2001 |
| DE | 19956509 A1 | 1/2001 |
| WO | WO 2012/076783 A1 | 6/2012 |
| WO | WO 2012/076783 A1 | 6/2012 |
| WO | WO 2018/104677 A1 | 6/2018 |
| WO | WO 2018/104677 A1 | 6/2018 |

OTHER PUBLICATIONS

Machine generated English language translation of WO2012/076783 (Year: 2022).*
Machine generated English language translation of DE19956509 (Year: 2022).*

* cited by examiner

*Primary Examiner* — Amy C Bonaparte
(74) *Attorney, Agent, or Firm* — Lynn B. Morreale

(57) ABSTRACT

The present invention relates to the use of a stabilizing composition comprising at least one N-oxyl compound and at least one polymerization inhibitor other than an N-oxyl compound, for inhibiting transesterification catalyst degradation in a process for the synthesis of aminoalkyl (meth) acrylates. Preferably, the transesterification catalyst is a titanium organometallic compound and the stabilising composition comprises at least one N-oxyl derivative and at least one polymerization inhibitor chosen from phenolic compounds and phenothiazine compounds in a weight ratio of between 1 and 10, preferably between 4 and 10, limits inclusive.

10 Claims, No Drawings

AMINOALKYL (METH)ACRYLATE STABILISATION

CROSS-REFERENCE TO RELATED APPLICATIONS

This application is a national stage application under 35 U.S.C. §371 of PCT/FR2019/052173, filed Sep. 18, 2019, which claims benefit to application FR 1859127, filed Oct. 2, 2018.

TECHNICAL FIELD

The present invention concerns the production of aminoalkyl (meth)acrylates by transesterification.

A more particular subject of the invention is the use of a stabilizing composition comprising at least one N-oxyl compound and at least one polymerization inhibitor selected from conventional polymerization inhibitors in a process for synthesizing aminoalkyl (meth)acrylates by transesterification, to inhibit both the breakdown of the transesterification catalyst and the radical polymerization of the aminoalkyl (meth)acrylate.

PRIOR ART AND TECHNICAL PROBLEM

It is known practice to prepare the (meth)acrylic esters of formula (I):

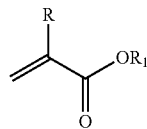
(I)

in which R is a hydrogen atom or a methyl group, and $R_1$ can be a linear or branched alkyl radical, or a cycloaliphatic, aryl, alkylaryl or arylalkyl radical, which may contain heteroatoms such as the nitrogen atom,
via a transesterification process by reaction of an alkyl (meth)acrylate of formula (II):

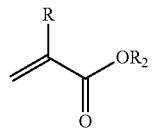
(II)

in which R is as defined above and $R_2$ can be a linear or branched alkyl group having from 1 to 4 carbon atoms, with an alcohol of formula (III):

$R_1$—OH (III)

in which $R_1$ is as defined above.

The transesterification reaction takes place in the presence of a transesterification catalyst, generally in the presence of an organometallic complex.

The implementation of such a process, however, is confronted with polymerization problems. It is a well-known fact, indeed, that one of the troublesome aspects in the manufacture and/or purification of (meth)acrylic monomers lies in the instability of these compounds and their ready tendency to evolve toward the formation of polymers. This evolution, caused by a radical reaction due to the effect of the temperature, is promoted particularly during steps in which these monomers are synthesized and purified, for example in the distillation steps. This results in the formation, in the plant apparatuses, of solid polymer deposits which end up causing blockages and make it necessary to shut down the plant for cleaning.

Polymerization inhibitors are therefore employed in order to stabilize the reaction medium in the processes for synthesizing (meth)acrylic esters, especially in the processes for synthesizing dialkylaminoalkyl (meth)acrylates by transesterification.

The conventional polymerization inhibitors are generally selected from N-oxyl compounds, such as 2,2,6,6-tetramethylpiperidine-N-oxyl and derivatives thereof, phenols or naphthols such as 2,6-tert-butyl-p-cresol, hydroquinone or the monomethyl ether of hydroquinone, aromatic amines such as N,N-diphenylamine, phosphorus compounds such as triphenyl phosphite, and sulfur compounds such as phenothiazine.

These compounds may be used alone or as a mixture, a particular instance being the use of phenothiazine in excess with 4-hydroxy-2,2,6,6-tetramethylpiperidine-N-oxyl (called 4-HT) as described in documents US 2004/0171868 and US 2004/0168903.

Document EP 467 850 recommends using a mixture of phenothiazine with an amine such as N,N-diethylhydroxylamine or N,N-di-tert-butylhydroxylamine to prevent clogging of apparatuses used in processes for synthesizing ethylenically unsaturated monomers.

N-Oxyl derivatives such as 2,2,6,6-tetramethylpiperidine-N-oxyl and derivatives thereof as polymerization inhibitors are renowned for their efficacy with (meth)acrylic monomers, which may be superior to the stabilizing efficacy of conventional polymerization inhibitors of the hydroquinone or phenothiazine variety.

Document DE19956509A1 illustrates the stabilizing properties of 4-hydroxy 2,2,6,6-tetramethylpiperidine-N-oxyl (4-HT) for inhibiting the polymerization of acrylic acid. This derivative may be used alone, or, when the process temperatures are high, in combination with phenothiazine so as to maintain high stability on the part of the inhibitor composition.

According to document EP 765 856, stabilized compositions of acrylic acid are obtained by means of a mixture of 4-hydroxy 2,2,6,6-tetramethylpiperidinyloxy (4-HT) and a phenol derivative such as hydroquinone methyl ether.

Document U.S. Pat. No. 5,322,960 describes the stabilization of (meth)acrylic acid and esters thereof by means of mixtures of an N-oxyl compound, a phenol compound, and a phenothiazine compound. The examples illustrate the use of 4-HT/hydroquinone/phenothiazine alone or in pairwise mixtures. This document teaches an improvement to the stabilization in the presence of the ternary mixture of stabilizers.

When an N-oxyl compound is used as sole polymerization inhibitor during the synthesis of aminoalkyl (meth)acrylates by transesterification reaction, the Applicant Company has observed the incidence of insoluble solid compounds in spite of the efficacy of such a compound in stabilization toward polymerization. These solids have been identified as inorganic salts arising from the breakdown of the transesterification catalyst. Formation of these solids causes fouling of the transesterification reactor, leading to maintenance works on an industrial production unit. It has been noted, moreover, that the activity of the organometallic complex employed as transesterification catalyst is lowered under these conditions, with a consequent drop in reaction yield.

Surprisingly, the inventors have found that this problem can be solved by combining the N-oxyl compound with at least a default amount of a polymerization inhibitor other than an N-oxyl compound. The inventors in effect have found that the combination of an N-oxyl compound with at least one polymerization inhibitor selected from the other conventional polymerization inhibitors enables not only inhibition of the reactions of radical polymerization during the synthesis of aminoalkyl (meth)acrylates by transesterification, but also prevention of breakdown on the part of the transesterification catalyst in organometallic complex form, and hence enables a high catalytic activity to be maintained during the synthesis, while reducing maintenance works in the production plant.

Although the prior art teaches combining an N-oxyl compound with a phenol compound such as hydroquinone and/or phenothiazine, as in documents EP 0765 856, EP 0620 206, and DE19956509 A1, this relates only to the stabilization of (meth)acrylic acids and their esters to radical polymerization leading to the formation of heavy byproducts. The problem linked to the breakdown of the catalyst during synthesis by transesterification is neither posed nor even suggested.

The present invention therefore provides a composition of polymerization inhibitors which is effective to prevent the formation of heavy byproducts arising from radical polymerization reactions while avoiding the breakdown of the catalyst during the synthesis of aminoalkyl (meth)acrylates by transesterification.

SUMMARY OF THE INVENTION

A subject of the invention is therefore the use of a stabilizing composition comprising at least one N-oxyl compound and at least one polymerization inhibitor other than an N-oxyl compound, for inhibiting the breakdown of the transesterification catalyst in a process for synthesizing aminoalkyl (meth)acrylates, by transesterification of an alkyl (meth)acrylate of formula (II):

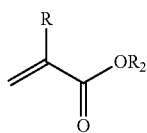

(II)

in which R is a hydrogen atom or a methyl group and $R_2$ can be a linear or branched alkyl group having from 1 to 4 carbon atoms, with an alcohol $R_1$—OH of formula (III):

HO-A-N(R'$_1$)(R'$_2$)    (III)

in which:
A is a linear or branched $C_1$-$C_5$ alkylene radical,
R'$_1$ and R'$_2$, which are identical or different from one another, represent a hydrogen atom or a $C_1$-$C_4$ alkyl radical. With preference, R'$_1$ and R'$_2$ represent a $C_1$-$C_4$ alkyl radical.

In one embodiment of the invention, the N-oxyl compound is selected from 2,2,6,6-tetramethylpiperidine 1-oxyl (called TEMPO), and derivatives thereof such as 4-hydroxy-2,2,6,6-tetramethylpiperidine 1-oxyl (4-OH-TEMPO or 4-HT), or 4-oxo-2,2,6,6-tetramethylpiperidine 1-oxyl (4-Oxo-TEMPO), and also a mixture of these compounds.

The N-oxyl compound is preferably 4-hydroxy-2,2,6,6-tetramethylpiperidine 1-oxyl (4-OH-TEMPO or 4-HT) (CAS Number 2226-96-2) with the following structure:

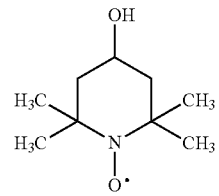

In one embodiment, the polymerization inhibitor is selected from phenol compounds and phenothiazine compounds.

The term "phenol compound" comprehends compounds derived from phenol, from naphthol, and quinones.

Phenol compounds include, but are not limited to, those in the following list: p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (or 2,6-tert-butyl-p-cresol) or 4-tert-butyl-2,6-dimethylphenol, hydroquinone (HQ), hydroquinone methyl ether (HQME).

The term "phenothiazine compound" comprehends phenothiazine and derivatives thereof, preferably phenothiazine (PTZ).

With preference, the stabilizing composition comprises at least one polymerization inhibitor selected from phenothiazine, 4-methyl-2,6-tert-butylphenol, hydroquinone, and hydroquinone methyl ether.

In one embodiment, the N-oxyl compound is in excess in the stabilizing composition.

In one embodiment, the mass ratio of the N-oxyl compound to the one or more polymerization inhibitors is between 1 and 10, preferably between 2 and 10, more preferentially between 4 and 10, more particularly between 5 and 10, the mass ratio being expressed with endpoints included.

In one embodiment, the transesterification catalyst is an organometallic complex based on a group IV metal. The group IV metal is preferably titanium.

In one embodiment, the transesterification catalyst conforms to one of the following formulas:

$M(OR_3)_4$ in which $R_3$ is a linear or branched $C_1$-$C_5$ alkyl radical and M is a group IV metal such as Ti, Zr, Hf.

$M\{OC(CH_3)=CH-C(CH_3)=O\}_4$ in which M is a group IV metal such as Ti, Zr, Hf.

Transesterification catalysts may include more particularly titanium alkoxides, such as tetraalkyl (ethyl, n-propyl, isopropyl, n-butyl) titanates, or Ti, Zr or Hf acetylacetonates.

According to the invention, the combination of a polymerization inhibitor with the N-oxyl compound makes it possible to inhibit the breakdown of the organometallic catalyst that is observed when the N-oxyl compound is used as sole polymerization inhibitor in a process for synthesizing aminoalkyl (meth)acrylates by transesterification, preferably in a process for synthesizing dialkylaminoalkyl (meth)acrylates by transesterification. It has been found, furthermore, that this combination is much more effective at inhibiting polymerization than the polymerization inhibitor alone.

A further subject of the invention relates to a process for synthesizing aminoalkyl (meth)acrylates, by transesterification of an alkyl (meth)acrylate of formula (II):

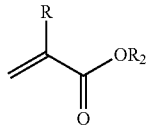
(II)

in which R is a hydrogen atom or a methyl group and $R_2$ can be a linear or branched alkyl group having from 1 to 4 carbon atoms,
with an alcohol $R_1$—OH of formula (III):

HO-A-N(R'$_1$)(R'$_2$) (III)

in which:
A is a linear or branched $C_1$-$C_5$ alkylene radical,
R'$_1$ and R'$_2$, which are identical or different from one another, represent a hydrogen atom or a $C_1$-$C_4$ alkyl radical. With preference, R'$_1$ and R'$_2$ represent a $C_1$-$C_4$ alkyl radical,
in the presence of a transesterification catalyst selected from organometallic compounds conforming to one of the following formulas:
$M(OR_3)_4$ in which $R_3$ is a linear or branched $C_1$-$C_5$ alkyl radical and M is a group IV metal such as Ti, Zr, Hf,
$M\{OC(CH_3)=CH-C(CH_3)=O\}_4$ in which M is a group IV metal such as Ti, Zr, Hf,
characterized in that the transesterification is carried out in the presence of a stabilizing composition comprising at least one N-oxyl derivative and at least one polymerization inhibitor selected from phenol compounds and phenothiazine compounds in a mass ratio of between 1 and 10, preferably between 2 and 10, more preferentially between 4 and 10, more particularly between 5 and 10, the mass ratio being expressed with endpoints included.

In the present invention, "stabilizing composition" signifies that the secondary reactions of radical polymerization and also the decomposition of the metal catalyst are inhibited in the reaction mixture in the presence of said stabilizing composition.

The invention hence provides an aminoalkyl (meth)acrylate synthesis process that is able to operate continuously over a long duration with no loss in catalyst efficacy or need for reactor cleaning.

The invention is now described in greater detail and in a nonlimiting manner in the description that follows.

DETAILED ACCOUNT OF THE INVENTION

The invention relates to the synthesis of aminoalkyl (meth)acrylates of formula (I):

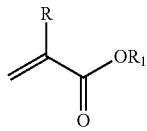
(I)

via transesterification reaction of an alkyl (meth)acrylate of formula (II):

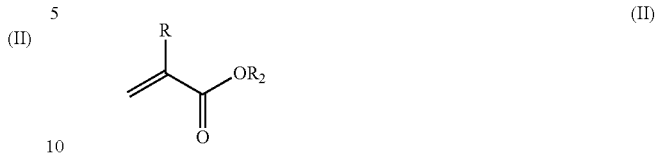

with an alcohol of formula: $R_1$—OH,
in which R, $R_1$ and $R_2$ are as defined above.
The term "(meth)acrylic" means acrylic or methacrylic; the term "(meth)acrylate" means acrylate or methacrylate.
Possible examples of alcohol $R_1$—OH include N,N-dimethylaminoethanol (DMAE), N,N-diethylaminoethanol, N,N-dimethylaminopropanol, 2-aminoethanol, and 2-methylaminoethanol.

The alcohol $R_1$OH is preferably a dialkylamino alcohol of formula (III):

HO-A-(R'$_1$)(R'$_2$) (III)

in which:
A is a linear or branched $C_1$-$C_5$ alkylene radical,
R'$_1$ and R'$_2$, which are identical or different from one another, represent a hydrogen atom or a $C_1$-$C_4$ alkyl radical. With preference, R'$_1$ and R'$_2$ represent a $C_1$-$C_4$ alkyl radical,
Preferably, the alcohol $R_1$—OH is N,N-dimethylaminoethanol (DMAE), also hereinafter called dimethylaminoethanol.

Preferably, the alkyl (meth)acrylate of formula (II) is methyl acrylate or ethyl acrylate, more preferentially ethyl acrylate.

In one embodiment, the invention pertains to the synthesis of dimethylaminoethyl acrylate (DMAEA) by transesterification reaction of ethyl acrylate (EA) with dimethylaminoethanol.

The transesterification catalyst is an organometallic complex, used generally in an amount that may range from 0.001 to 0.02 mol, preferably from 0.005 to 0.01 mol, per mole of alcohol $R_1$—OH.

The transesterification catalyst is preferably an organometallic complex based on titanium.

The reaction temperature is generally between 80 and 150° C. and the pressure is generally maintained at between 0.5 and 1.1 bar. The reaction temperature is preferably between 90 and 130° C. and the pressure is of the order of 0.65 bar to atmospheric pressure.

According to the invention, the stabilizing composition comprising at least one N-oxyl derivative and at least one polymerization inhibitor other than an N-oxyl derivative enables the secondary reactions of radical polymerization during the synthesis to be prevented while avoiding the breakdown of the catalyst into insoluble salts.

The stabilizing composition is generally introduced into the transesterification reactor in the form of a solution in the alkyl (meth)acrylate (II), in a proportion of 100 to 5000 ppm, preferably between 500 and 3000 ppm, relative to the initial charge of reactants.

The N-oxyl compound is preferably in excess in the stabilizing composition; generally, the amount by mass of N-oxyl compound is more than 50%, preferably more than 80%, and may be from 80% to 95% relative to the stabilizing composition.

The advantage endowed by the invention is that of using a more highly performing stabilizing composition than a polymerization inhibitor alone in the stabilization of (meth) acrylic monomers, with no adverse effect on the process by transesterification.

The examples below illustrate the present invention without, however, limiting the scope thereof.

EXPERIMENTAL SECTION

In the examples below, all of the concentrations are given in mass % and ppm by mass unless stated otherwise, and the abbreviations used are as follows:
EA: Ethyl acrylate
DMAE: Dimethylaminoethanol
DMAEA: Dimethylaminoethyl acrylate
PTZ: Phenothiazine
4-HT: 4-OH-TEMPO
HQME: Hydroquinone methyl ether
Ti(OEt)$_4$: Tetraethyl titanate
TOF: Turn-over frequency
MIS: Matter in suspension The protocol used for all of the inventive examples and comparative examples was as follows:

A stirred 0.5 L reactor, heated by circulation of thermostated oil at 135° C. within a jacket, surmounted by a distillation column with Multiknit packing, with a condenser containing water-glycol mixture at the column top, a reflux head, a vacuum separator, receivers and traps, is fed continuously with the EA, the heavy alcohol (DMAE), and a transesterification catalyst (Ti(OEt)$_4$).

The polymerization inhibitors (PTZ, 4-HT, EMHQ or a mixture of these compounds) are injected continuously as a mixture with the EA.

Throughout the synthesis, air is sparged into the reaction mixture. The reaction is carried out at a temperature of 119-121° C. under a reduced pressure of 860 to 870 mm Hg.

The ethanol formed during the reaction is removed at the rate it is formed, as an EA/ethanol azeotrope.

The conversion rate is monitored by refractometric analysis of the azeotrope. The ethanol content is between 58% and 62%.

The crude reaction mixture is withdrawn using an overflow and recovered in a receiver, for analysis after 120 h of operation.

The bottom and distillate streams were analyzed by gas chromatography, to ascertain the yield of desired ester and the conversion of the heavy alcohol.

The inhibitors were analyzed and quantified by liquid chromatography.

The heavy impurities (catalyst+heavy byproducts formed) were quantified using a thermal balance.

On the basis of these analyses, the catalytic activity after 120 h is also determined by the value of the TOF, calculated according to the formula below. The residence time Rt is determined according to the extraction flow rate at the bottom of the transesterification reactor.

$$TOF = \frac{N_{DMAEA} \text{ (moles)}}{N_{Catalyst} \text{ (moles)} \times Rt}$$

Tests in accordance with the invention were performed using a polymerization inhibitor in the form either of a mixture of 4-HT and PTZ with excess 4-HT (Examples 1 to 3) or a mixture of 4-HT and HQME with excess 4-HT (Example 4).

For comparison, tests were carried out with 4-HT alone (Example 5), PTZ alone (Example 6), or a mixture of 4-HT and PTZ with excess PTZ (Example 7).

For all of the tests in accordance with the invention (Examples 1 to 4), the reactor remained completely clear after 120 h of operation, with no observed reactor fouling.

The comparative tests carried out with 4-HT alone (Ex 5) showed incidence of a white inorganic compound accumulating during the synthesis, with reactor fouling from 24 h of operation and loss of catalyst activity.

The comparative tests carried out with PTZ alone (Ex 6) or a mixture of 4-HT and PTZ with excess PTZ (Ex 7) showed more substantial formation of soluble polymers (heavies >1.0%) in the transesterification reactor.

The results of these tests are collated in Table 1 below.

TABLE 1

|  |  | Ex 1 | Ex 2 | Ex 3 | Ex 4 | Ex 5 comp. | Ex 6 comp. | Ex 7 comp. |
|---|---|---|---|---|---|---|---|---|
| FEED | EA (g/h) | 61.8 | 62.2 | 62.2 | 61.5 | 62.0 | 59.9 | 59.9 |
|  | DMAE (g/h) | 34.3 | 34.5 | 34.5 | 34.2 | 34.4 | 33.3 | 33.3 |
|  | Ti(OEt)$_4$ (g/h) | 1.2 | 1.2 | 1.2 | 1.2 | 1.2 | 1.2 | 1.2 |
| STAB | PTZ (g/h) | 0.004 | 0.008 | 0.020 | — | — | 0.05 | 0.05 |
|  | HQME (g/h) | — | — | — | 0.008 | — | — | — |
|  | 4-HT (g/h) | 0.039 | 0.041 | 0.040 | 0.040 | 0.040 | — | 0.012 |
| RESULTS | Conversion (%) | 83.0 | 83.7 | 83.2 | 79.9 | 83.5 | 83.1 | 83.0 |
|  | Yield (%) | 84.1 | 84.2 | 84.3 | 83.0 | 81.6 | 82.8 | 82.9 |
|  | TOF (h$^{-1}$) | 18.1 | 17.8 | 17.8 | 19.1 | 15.9 | 16.7 | 17.1 |
|  | Heavies (%) | 0.7 | 0.8 | 0.6 | 0.9 | 1.0 | 1.4 | 1.6 |
|  | Fouling (h) | >120 | >120 | >120 | >120 | 24 | >120 | >120 |
|  | Reactor appearance | clear | clear | clear | clear | MIS | clear | clear |

The invention claimed is:

1. A process for synthesizing aminoalkyl (meth)acrylates, comprising the step of transesterifying an alkyl (meth)acrylate of formula (II):

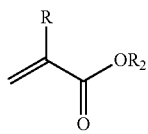 (II)

in which R is a hydrogen atom or a methyl group and $R_2$ is a linear or branched alkyl group having from 1 to 4 carbon atoms,
with an alcohol R1-OH of formula (III):

 (III)

in which
A is a linear or branched $C_1$-$C_5$ alkylene radical,
R'1 and R'2, which are identical or different from one another, represent a hydrogen atom or a $C_1$-$C_4$ alkyl radical,
in the presence of a transesterification catalyst selected from the group consisting of organometallic compounds of one of the following formulas:
M(OR3)$_4$ in which R3 is a linear or branched $C_1$-$C_5$ alkyl radical and M is a group IV metal or,
M{OC(CH3)=CH—C(CH3)=O}$_4$ in which M is a group IV metal, whereby the transesterification is carried out in the presence of a stabilizing composition comprising at least one N-oxyl compound and at least one polymerization inhibitor selected from the group consisting of phenol compounds and phenothiazine compounds in a mass ratio of between 1 and 10, endpoints included.

2. The process as claimed in claim 1, wherein the aminoalkyl (meth)acrylate is dimethylaminoethyl acrylate.

3. The process as claimed in claim 1, in which the N-oxyl compound is selected from the group consisting of 2,2,6,6-tetramethylpiperidine 1-oxyl (TEMPO), 4-hydroxy-2,2,6,6-tetramethylpiperidine 1-oxyl (4-OH-TEMPO), 4-oxo-2,2,6,6-tetramethylpiperidine 1-oxyl (4-Oxo-TEMPO), and mixtures thereof.

4. The process as claimed in claim 1 in which the stabilizing composition comprises at least one polymerization inhibitor selected from the group consisting of phenothiazine, 4-methyl-2,6-tert-butylphenol, hydroquinone, and hydroquinone methyl ether.

5. The process as claimed in claim 1 in which the mass ratio of the N-oxyl compound to the one or more polymerization inhibitors is between 2 and 10, endpoints included.

6. The process as claimed in claim 1 in which the mass ratio of the N-oxyl compound to the one or more polymerization inhibitors is between 4 and 10, endpoints included.

7. The process as claimed in claim 1 in which the mass ratio of the N-oxyl compound to the one or more polymerization inhibitors is between 5 and 10, endpoints included.

8. The process as claimed in claim 1 in which the alcohol R1-OH is dimethylaminoethanol.

9. The process as claimed in claim 1 in which said group IV metal M is titanium.

10. The process as claimed in claim 1 in which said transesterification catalyst is selected from the group consisting of titanium alkoxides, tetraalkyl titanates, and Ti, Zr or Hf acetylacetonates.

* * * * *